(12) United States Patent
Moret et al.

(10) Patent No.: US 9,399,613 B2
(45) Date of Patent: Jul. 26, 2016

(54) DIRECT CARBON DIOXIDE HYDROGENATION TO FORMIC ACID IN ACIDIC MEDIA

(71) Applicant: EOS Holding SA, Lausanne (CH)

(72) Inventors: Severine Moret, Vevey (CH); Paul Joseph Dyson, Lonay (CH); Gabor Laurenczy, Lonay (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 14/768,102

(22) PCT Filed: Feb. 10, 2014

(86) PCT No.: PCT/IB2014/058883
§ 371 (c)(1),
(2) Date: Aug. 14, 2015

(87) PCT Pub. No.: WO2014/125409
PCT Pub. Date: Aug. 21, 2014

(65) Prior Publication Data
US 2016/0016875 A1    Jan. 21, 2016

(30) Foreign Application Priority Data

Feb. 15, 2013 (EP) ..................... 13155490

(51) Int. Cl.
*C07C 53/02* (2006.01)
*C07C 51/00* (2006.01)

(52) U.S. Cl.
CPC ..................... *C07C 51/00* (2013.01)

(58) Field of Classification Search
CPC .............................. C07C 53/02; C07C 51/15
USPC .......................................... 562/609
See application file for complete search history.

(56) References Cited

PUBLICATIONS

International Search Report; European Patent Office; International PCT Application No. PCT/IB2014/058883; May 16, 2014; 2 pages.
Ferenc Joo et al., Homogeneous Hydrogenation of Aqueous Hydrogen Carbonate to Formate Under Exceedingly Mild Conditions—A Novel Possibility of Carbon Dioxide Activation, ChemComm, 1999, pp. 971-972.
Philip G. Jessop, Homogeneous Hydrogenation of Carbon Dioxide, The Handbook of Homogeneous Hydrogenation, Copyright 2007 WILEY-VCH Verlag GmbH & Co. KGaA, Weinheim, ISBN: 978-3-527-31161-3, pp. 489-511.

*Primary Examiner* — Jafar Parsa
(74) *Attorney, Agent, or Firm* — Taft Stettinius & Hollister LLP

(57) ABSTRACT

The present invention relates to a method of producing formic acid in a catalyzed chemical reaction from hydrogen gas and carbon dioxide gas, said reaction being conducted in an acidic medium comprising a polar solvent over a wide range of temperatures at total gas pressure of hydrogen and carbon dioxide up to 250 bar without the addition of base, carbonate, hydrogen carbonate or formate. The method of the present invention is advantageous since the reaction may be conducted in a polar solvent such as water or DMSO.

9 Claims, 5 Drawing Sheets

DIRECT CARBON DIOXIDE HYDROGENATION TO FORMIC ACID IN ACIDIC MEDIA

CROSS-REFERENCE TO RELATED APPLICATIONS

The present application is a U.S. national stage filing of International Application No. PCT/IB2014/058883 filed Feb. 10, 2014, which claims priority to European Patent Application No. 13155490.9 filed Feb. 15, 2013, the contents of each application incorporated herein by reference in its entirety.

TECHNICAL FIELD

The present invention relates to a method of producing formic acid only from hydrogen gas and carbon dioxide in acidic medium, namely to a method of producing formic acid in a catalysed chemical reaction from hydrogen gas and carbon dioxide in acidic medium without any additives, such as base, salts amines, formate, hydrogen carbonate and carbonate.

PRIOR ART AND THE PROBLEM UNDERLYING THE INVENTION

Dihydrogen or hydrogen gas ($H_2$) is among the candidates as an energy carrier or fuel because it can be converted efficiently to electricity without producing toxic products or greenhouse gases.

However, hydrogen gas has extremely low density (0.08 g/L). On an industrial scale and industrial applications, $H_2$ is constrained by its physical properties, leading to safety concerns, transport problems and a low energy density. As a consequence, hydrogen gas is stored at high pressure or low temperature in gas containers made of steel, the weight of which far exceeds the weight of the hydrogen gas stored in it. Further, hydrogen gas reacts violently with oxygen or air in a wide concentration range, making the storage of large quantities of hydrogen dangerous.

Nonetheless, liquids with high density content of hydrogen can be safe to handle. They offer greater energy density and can be easily transported using the existing infrastructure for gasoline and oil. Therefore, formic acid due to its high volumetric hydrogen density, low-toxicity and easy handling is considered as a material of choice for the storage of hydrogen.

It is an objective to provide a process for hydrogen storage and generation, which enables the construction of a practical charge/discharge device. The hydrogen storage/discharge device is rechargeable by a process of direct hydrogenation of carbon dioxide into formic acid in acidic medium without using any additives.

Formic acid or formate salts can be generated by catalytic reduction or hydrogenation of carbon dioxide, carbonate or bicarbonate in the presence of organic solvents, in biphasic systems, in ionic liquids, in aqueous solution and in supercritical $CO_2$, with noble-metals, such as ruthenium, rhodium and iridium as catalysts as well with iron, in neutral or basic media. This reaction is endergonic in gaseous phase. In aqueous solution, this reaction is exothermic and exergonic and is performed in the presence of added base resulting in the formation of formates (salts of the formic acid), of formic acid adducts with amines. Said reactions are performed at pH 6 to 14. At such pH, the real substrate for the hydrogenation is bicarbonate or carbonate and not carbon dioxide, which does not correspond to a direct hydrogenation process of carbon dioxide gas to produce formic acid. To separate the obtained formic acid, the base used for the hydrogenation has to be neutralized by acidifying the medium with a high quantity of acid, which is very costly at an industrial scale. Moreover, to yield to formic acid product, further steps of separation are required to remove salts and amines adducts, which are also not costly effective (A. Boddien, F. Gartner, C. Federsel, P. Sponholz, D. Mellmann, R. Jackstell, H. Junge, M. Beller, Angew Chem Int Ed 2011, 50, 6411; D. Preti, S. Squarcialupi, G. Fachinetti, Angew Chem Int Ed 2010, 49, 2581; T. Schaub, R. A. Paciello, Angew Chem Int Ed 2011, 50, 7278).

Hull and co-workers have developed a process of reversible $H_2$ storage, which involves a pH-modulated catalyst driving actually the hydrogenation of bicarbonate into formate, since the process takes place under basic conditions. The hydrogen is easily triggered by acidifying the solution to protonate the catalyst. The change of the pH is required in this process to switch from the reaction of producing formate, due to the hydrogenation of carbonate or bicarbonate, to the reaction of $H_2$ delivery (J. F. Hull, Y. Himeda, W.-H. Wang, B. Hashiguchi, R. Periana, D. J. Szalda, J. T. Muckerman, E. Fujita, Nat Chem. 2012, 4, 383).

The main drawback of this multistep process for an industrial application is the production of high quantity of salt resulting from the pH shifting and the bad recycling of the catalyst. Furthermore, this process requires the separation of formed formic acid from the resulting salts and adducts, which is not economically trivial. Such processes are not proper to be exploited into a hydrogen storage/discharge device as described above.

The development of a process to perform the carbon dioxide hydrogenation under the same acidic conditions as the condition of the reaction of hydrogen delivery is particularly needed in order to avoid any further steps of acidification and purification, which are not economic in a reversible hydrogen storage system.

Ogo and co-workers have developed a catalysed process of carbon dioxide hydrogenation under acidic aqueous conditions with ruthenium and iridium arene compounds as catalysts (S. Ogo, R. Kabe, H. Hayashi, R. Harada, S. Fukuzumi, *Dalton Trans* 2006, 4657; H. Hayashi, S. Ogo, T. Abura, S. Fukuzumi, *J Am Chem Soc* 2003, 125, 14266; Y. Himeda, Advances in $CO_2$ Conversion and Utilization 2010, 1056, 141; G. Laurenczy, Chimia 2011, 65, 663). In these processes, it is rather bicarbonate ($HCO_3^-$), which is the real substrate of the hydrogenation of these catalysed systems using transition metal hydride complexes in water such as ruthenium or iridium complexes. Although the reaction is still conducted in acidic medium, the pH varies. However, new catalysts for catalysed hydrogenation of $CO_2$ in water and acidic conditions are still needed for the construction of new $CO_2$ reduction system in polar solvents.

In view of the above-mentioned prior art, the present invention addresses the problem to improve the process of formic acid production from direct hydrogenation of carbon dioxide in acidic reaction medium to obtain formic acid without the need of any additives such as base, amines, formate, hydrogen carbonate or carbonate additives and without the formation of salts because of the presence of added bases. The resulting produced formic acid is pure, namely without any adducts and may be directly available and suitable for further use without any further steps of purification or separation from the adducts or the additives present in the reaction.

It is an objective of the present invention to provide a process of formic acid production from direct carbon dioxide hydrogenation in acidic medium comprising at least one polar solvent, having an improved yield of produced formic acid without any formate or carbonate additives and the addition of bases; using water soluble ruthenium(II), rhodium(I), iridium(III) or Fe phosphine catalyst systems and at mid pressure conditions.

It is also an objective of the present invention to provide a process of formic acid production from direct carbon dioxide hydrogenation in acidic medium having an improved yield of produced formic acid with a high efficiency rate, a good recyclability of the catalyst and which may be suitable for a hydrogen storage/discharge device involving a continue process of hydrogen storage under the form of formic acid, which is pure and without any adducts to be readily available and suitable for further use or process, such as the process of producing hydrogen or of producing electricity.

The present invention addresses the problems depicted above, which are part of the invention.

SUMMARY OF INVENTION

The inventors of the present invention provided a method for producing formic acid from hydrogen gas and carbon dioxide gas, which method meets the objectives discussed above and which solves the problems of the prior art.

In an aspect, the present invention relates to a method for producing formic acid in a catalysed chemical reaction from hydrogen gas and carbon dioxide gas, said reaction being conducted in an acidic medium comprising at least one polar solvent; without any addition of a base and of at least a compound selected from formate ($HCOO^-$), carbonate ($CO_3^{2-}$), hydrogen carbonate ($HCO_3^-$) or any salt thereof; at a temperature in the range of 15-140° C.; at a total gas pressure of hydrogen gas and carbon dioxide gas being in the range of 30 to 250 bar; in the presence of a catalyst, said catalyst comprising a complex of the general formula (I):

$$MR_n(L1)_m(L2)_p \qquad (I)$$

wherein, M is a metal selected from Ru, Rh, Ir or Fe; R is Cl or $H_2O$; L1 is an imidazolium pincer ligand or a ligand comprising at least one phosphorus atom, said phosphorus atom being bound by a complex bond to said metal, the phosphorus ligand further comprising at least an aromatic group and a hydrophilic group, or a cycloalkane group; L2 is a ligand selected from tri-ethylene trisulfide, dimethylbenzylamine or para-cymene; n, m and p are integer, wherein n is 1 or 2, m is in the range of 1-4 and p is in the range of 0-1; and wherein the complex of formula (I) optionally comprises other ligands and is provided in the form of a salt or is neutral.

Further aspects and preferred embodiments of the invention are defined herein below and in the appended claims.

The catalysed reaction of the production of formic acid from direct hydrogenation of carbon dioxides takes place in an acidic medium comprising at least one polar solvent at relatively low temperatures. The method of the present invention is believed to be highly advantageous because said reaction can be conducted already in a polar solvent such as in water being an environmentally friendly, cheap and abundant solvent, or in DMSO, and provides a high yield of produced formic acid from direct hydrogenation of carbon dioxide, said yield of formic acid corresponding to a turnover number (TON) up to 1000, without the addition of any formate, hydrogen carbonate or carbonate additives and of any bases. This yield is at least about 50 times higher than yield obtained until nowadays in a method of homogeneous hydrogenation of carbon dioxide in pure aqueous acidic solution, namely acidic solution comprising water, without the need of any formate or carbonate additives and/or of any bases.

The catalyst in the method of the present invention is recycled without any addition of base or acid and the equilibrium of the reaction is reached in an acidic medium comprising at least one polar solvent, namely water or DMSO after about one day and a half, at low temperatures.

Taking into account all the above-described features and advantages render the method of the present invention an extremely valuable tool for producing formic acid, namely free formic acid, directly without any additives: carbonate, or formate, salts and/or bases and for further generating hydrogen gas from the formic acid obtained by the method of invention, for any purpose one can envisage, such as energy or electricity.

Further features and advantages of the invention will also become apparent to the skilled person from the description of the preferred embodiments given below.

DETAILED DESCRIPTION

Figure 1:
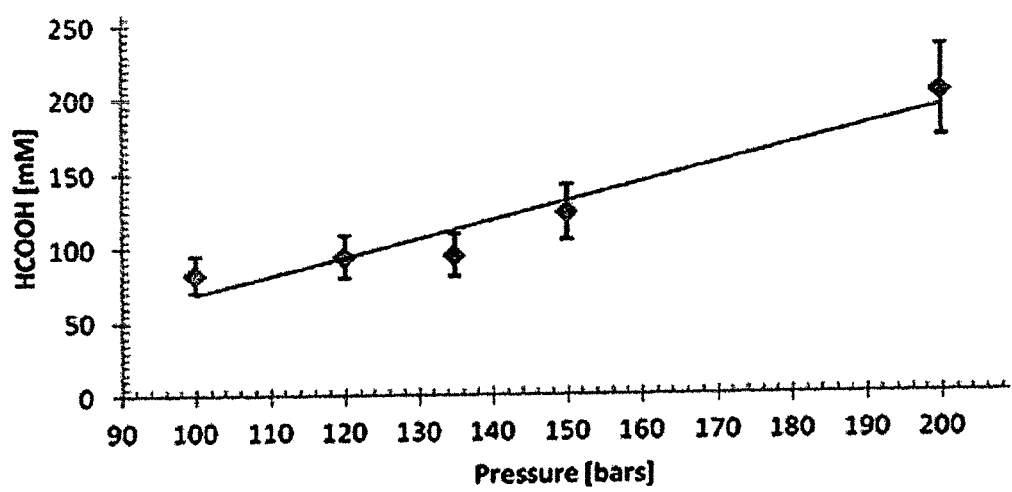
FIG. 1 shows the pressure dependence of the catalytic hydrogenation of $CO_2$ in water using [$RuCl_2(PTA)_4$] catalyst.

The present invention provides a method to generate formic acid in a catalysed chemical reaction from direct hydrogenation of carbon dioxide in acidic medium in the absence of any added formate ($HCOO^-$) or carbonate ($CO_3^{2-}$), hydrogen carbonate ($HCO_3^-$) and any salt thereof, and in the absence of any bases or any salt thereof. The method of the invention provides a significant production yield of formic acid under acidic reaction conditions, wherein the rate and the yield of the formic acid product can be controlled by varying the total hydrogen gas and carbon dioxide gas pressure during the reaction and/or by varying the temperature of the reaction.

The present invention also provides a method for producing formic acid in a catalysed chemical reaction from hydrogen gas and carbon dioxide gas, said reaction being conducted in an acidic medium comprising at least one polar solvent; without any addition of a base and of at least a compound selected from formate ($HCOO^-$), carbonate ($CO_3^{2-}$), hydrogen carbonate ($HCO_3^-$) and any salt thereof;

at a temperature in the range of 15-140° C.; and at a total gas pressure of hydrogen and carbon dioxide being in the range of 30 to 250 bar.

In particular, the present invention provides a method of producing formic acid in a catalysed chemical reaction from hydrogen gas and carbon dioxide gas, said reaction being conducted in an acidic medium comprising at least one polar solvent, without any addition of a base and of at least a compound selected from formate (HCOO$^-$), carbonate (CO$_3^{2-}$), hydrogen carbonate (HCO$_3^-$) and any salt thereof, at a temperature in the range of 15-140° C., at a total gas pressure of hydrogen and carbon dioxide being in the range of 30 to 250 bar, in the presence of a catalyst, said catalyst comprising a complex of the general formula (I):

$$MR_n(L1)_m(L2)_p \qquad (I),$$

wherein,
M is a metal selected from Ru, Rh, Ir, or Fe, R is Cl or H$_2$O;
L1 is an imidazolium pincer ligand or a ligand comprising at least one phosphorus atom, said phosphorus atom being bound by a complex bond to said metal, the phosphorus ligand further comprising at least an aromatic group and a hydrophilic group, or a cycloalkane group;
L2 is a ligand selected from tri-ethylene trisulfide, dimethylbenzylamine or para-cymene; n, m and p are integer, wherein n is 1 or 2, m is in the range of 1-4 and p is in the range of 0-1;
and wherein the complex of formula (I) optionally comprises other ligands and is provided in the form of a salt or is neutral.

In particular, the present invention also provides a method for producing formic acid in a catalysed chemical reaction from hydrogen gas and carbon dioxide gas, said reaction being conducted in an acidic medium comprising at least one polar solvent; at a temperature in the range of 15-140° C.; at a total gas pressure of hydrogen and carbon dioxide being in the range of 30 to 250 bar; in the presence of a catalyst, said catalyst comprising a complex of the general formula (I):

$$MR_n(L1)_m(L2)_p \qquad (I)$$

wherein,
M is a metal selected from Ru, Rh, Ir or Fe;
R is Cl or H$_2$O;
L1 is an imidazolium pincer ligand or a ligand comprising at least one phosphorus atom, said phosphorus atom being bound by a complex bond to said metal, the phosphorus ligand further comprising at least an aromatic group and a hydrophilic group, or a cycloalkane group;
L2 is a ligand selected from tri-ethylene trisulfide, dimethylbenzylamine or para-cymene;
n, m and p are integer, wherein n is 1 or 2, m is in the range of 1-4 and p is in the range of 0-1; and
wherein the complex of formula (I) optionally comprises other ligands and is provided in the form of a salt or is neutral.

The catalysed reaction is robust, as the catalyst comprising a complex of the general formula (I) is completely recycled and is effective for prolonged time without degradation. The catalyst preferably used in the method of the present invention is stable at the temperatures and in the acidic environment of the reaction.

The catalyst to be used in the reaction of the present invention is soluble in a polar solvent at least 10 g/L at 25° C. Of course, catalysts having lower solubility could do as well, for example with catalysts having higher efficiencies than those reported herein.

The catalyst is more soluble in the reaction medium, comprising at least one polar solvent, and in the product of the reaction, formic acid, than in the reactants, hydrogen gas and carbon dioxide gas.

Furthermore, the catalyst is stable at temperatures ≥60° C., ≥80° C., ≥120° C., more preferably ≥140° C. Stable, for the purpose of the present invention, means that the catalyst catalyses at least 10, preferably 30 or more reaction cycles without measurable degradation or measurable loss of activity.

The catalyst is stable at the pH, as defined further below, at which the reaction is conducted.

The catalyst of the method of the invention is preferably the complex of the general formula (I): $MR_n(L1)_m(L2)_p$ as defined above.

M is a metal selected from Ru, Rh, Ir or Fe, preferably Ru or Fe, more preferably Ru. Ru preferably is in the oxidation state Ru$^{II}$ during the reaction, however, Ru$^{III}$, which is more easily available, may also be used. It was observed that Ru$^{III}$ is converted to Ru$^{II}$ during the reaction.

In formula (I) above, R is Cl or H$_2$O.

In the method of the invention, the imidazolium pincer ligand may be selected from 1-methyl-3-(prop-2-enyl)-1H-imidazol-3-ium or 1-allyl-3-methyl-1H-imidazol-3-ium.

L1 in formula (I) may be an imidazolium pincer ligand.

In the method of the invention, L1 may be a ligand comprising at least one phosphorus atom, said phosphorus atom being bound by a complex bond to said metal, the phosphorus ligand further comprising at least an aromatic group and a hydrophilic group, or a cycloalkane group. Said phosphorus ligand may be selected from the phosphine ligands.

In another embodiment of the method of the invention, L1 in formula (I) is selected from a phosphine ligand. Said phosphine ligand comprises at least one phosphorus atom, being bound by a complex bond to the metal of the ligand. The phosphine ligand is selected from aryl phosphines, alkyl phosphines or cycloalkane phosphines. Preferably the phosphine ligand is selected from aryl phosphines or cycloalkane phosphines. Said phosphine ligands may be further substituted by a hydrophilic group selected from sulphonate, carboxylate and/or hydroxyl.

The aryl phosphines are preferably selected from mono-, di- or triaryl phosphine, which are further substituted by a hydrophilic group selected from sulphonate, carboxylate and/or hydroxyl. Preferably the aryl phosphines are selected from phenyl phosphines, diphenyl phosphines or triphenyl phosphines, which are further substituted by the same as defined above. The aryl phosphine is substituted in order to increase its solubility in at least one polar solvent or in a polar solvent selected from water or DMSO. Preferably, the aryl phosphine is substituted by a hydrophilic group being sulphonate and the aryl phosphine is selected from mono-, di- or trisulphonated aryl phosphine, preferably from mono-, di- and/or trisulphonated triphenylphosphine. Most preferably, the trisulphonated aryl phosphine is the trisulphonated triarylphosphine, wherein the solubility in water is highest. The sulfonyl group may be in the meta or para position of the aryl/phenyl group bound to the phosphorus atom. Sulphonated triphenylphosphines with the sulfonate group present at the meta position are more easy to synthesise and are, therefore, preferably used in the method of the present invention.

The cycloalkane phosphine are selected from unsubstituted or substituted cycloalkane phosphine, preferably from adamantylphosphine optionally comprising further at least one heteroatom selected from N or O, most preferably from 1,3,5-triaza-7-phosphaadamantane (PTA). The cycloalkane phosphine, adamantylphosphine or PTA may be further substituted by alkyl, aryl, alkenyl, halo or hydroxyl group. A preferred substituted PTA is 3-methyl-1,3,7-triaza-5-phosphabicyclo[3.3.1]nonane (MePTA).

In an embodiment, L1 is at least one ligand selected from adamantylphosphines comprising further at least one heteroatom selected from N or O, or from mono-, di- or trisulphonated triphenylphosphine. Said adamantylphosphines may be further substituted as above.

L1 is at least one ligand selected from 1,3,5-triaza-7-phosphaadamantane (PTA), substituted PTA, 3-methyl-1,3,7-triaza-5-phosphabicyclo[3.3.1]nonane (MePTA) or from mono-, di- or trisulphonated triphenylphosphine.

L1 is at least one ligand selected from 1,3,5-triaza-7-phosphaadamantane (PTA), substituted PTA, 3-methyl-1,3,7-triaza-5-phosphabicyclo[3.3.1]nonane (MePTA); meta-monosulfonated triphenylphosphine (TPPMS) or meta-trisulfonated triphenylphosphine (TPPTS).

In an embodiment, L1 is at least one ligand selected from meta-monosulfonated triphenylphosphine (TPPMS), meta-trisulfonated triphenylphosphine (TPPTS), 1,3,5-triaza-7-phosphaadamantane (PTA), and 3-methyl-1,3,7-triaza-5-phosphabicyclo[3.3.1]nonane (MePTA). Preferably L1 is at least one ligand selected from PTA, MePTA or TPPMS.

L2 in the catalyst of formula (I) is present or absent. But, if present L2 is at least one ligand selected from tri-ethylene trisulfide ([9]aneS$_3$) or dimethylbenzylamine (C$_6$H$_5$(C$_3$H$_8$N)) or para-cymene.

m is 1, 2, 3 or 4 and p is 0 or 1, more preferably it is 1, 2 or 3. If m >1 and/or p >1, each L1 may be different from another L1 and/or each L2 may be different form another L2. Thus, if m is ≥2 and p is 0, each ligand L1$_{(1\ to\ m)}$ may be the same or different and L2$_{(p=0)}$ is absent.

Preferably, if M is Ru, n=2 or 4, m=2 or 4 and p=0, all ligands L1 are the same and are selected from cycloalkane phosphines or from aryl phosphines, most preferably from cycloalkane phosphines or from substituted admantylphosphines, alternatively, from 1,3,5-triaza-7-phosphaadamantane (PTA), 3-methyl-1,3,7-triaza-5-phosphabicyclo[3.3.1]nonane (MePTA). If M is Ru, preferably n is 2, m is 4 and p is o, i.e. ligand L2 is absent, and L1 is PTA.

An unlimited number of combinations are technically possible in the context of the present invention. Care has to be taken that, when selecting ligands, the preferred water, DMSO or polar solvents solubility of the ligand as defined herein is obtained.

According to another embodiment, the catalyst is selected from [RuCl$_2$(PTA)$_4$], [RhCl(PTA)$_3$], [RhCl(TPPMS)$_3$], [RuCl$_2$(PTA)([9]aneS$_3$)], [RuCl$_2$(PTA)(C$_6$H$_5$(C$_3$H$_8$N))], [RuCl$_2$(TPPMS)$_2$], [RuCl$_2$(TPPTS)$_2$] or [Ru(H$_2$O)$_4$(MePTA)$_2$](tos)$_4$. Preferably the catalyst is selected from [RuCl$_2$(PTA)$_4$], [RuCl$_2$(PTA)([9]aneS$_3$)], [RuCl$_2$(PTA)(C$_6$H$_5$(C$_3$H$_8$N))], [Ru(H$_2$O)$_4$(MePTA)$_2$](tos)$_4$ or [RuCl$_2$(TPPMS)$_2$]. Most preferably the catalyst is selected from [RuCl$_2$(PTA)$_4$], [RuCl$_2$(PTA)(C$_6$H$_5$(C$_3$H$_8$N))] or [Ru(H$_2$O)$_4$(MePTA)$_2$](tos)$_4$.

The catalyst may be provided in the form of a salt, wherein the complex of general formula (I) corresponds to formula (II):

$$[MR_n(L1)_m(L2)_p]X_y \qquad (II),$$

wherein X is a non coordinating anion, for example tosylate (tos), triflate, and Y is 1, 2, 3 or 4.

The catalyst is dissolved in the acidic medium of the reaction at a concentration in the range of 0.10 mM to 30.00 mM, in the preferred range of 0.60 mM to 10.00 mM, of 2.00 mM to 4.00 mM, of 2.50 mM to 3.00 mM. Preferably the concentration of the catalyst is 2.76 mM.

The catalysed reaction of the present invention takes place in an acidic medium comprising at least one polar solvent. The catalysed reaction of the present invention is preferably conducted in an acidic medium comprising at least one polar solvent, or if more than one polar solvent are present, a combination thereof. The polar solvent in the method of the invention is selected from water, DMSO, methanol, ethanol, acetonitrile, propylene carbonate, tetrahydrofurane, ionic liquids or a combination thereof. The polar solvent of the method of the invention is preferably selected from water or DMSO, and most preferably is DMSO. Water as polar solvent for the purpose of the invention includes also degassed water. The ionic liquids are selected from imidazolium ionic liquids and salts thereof, e.g. tosylate, tetrafluoroborate. The ionic liquids as polar solvents of the method of the invention are selected from butyl-methylimidazolium (BMIM) and salts thereof, preferably selected from butyl-methylimidazolium, butyl-methylimidazolium tetrafluoroborate, butyl-methylimidazolium tosylate.

In one embodiment the method of the invention is conducted in an acidic medium comprising a polar solvent being water.

In a further embodiment, the method of the invention is conducted in an acidic medium comprising a polar solvent being DMSO.

In a further embodiment, the method of the invention is conducted in an acidic medium of comprising two polar solvents as defined above. Preferably the two polar solvents are water and DMSO. Preferably the ration water:DMSO is in the range 1:4 to 1:9.

To carry out the catalysed reaction of the method of the invention, only the starting material hydrogen gas and carbon dioxide and the catalyst dissolved in a polar solvent, preferably preferably water or DMSO, are required. No further additives such as base, base salts, formate or carbonate or hydrogen carbonate is necessary to carry out said reaction.

The catalysed reaction of the method of the invention is conducted at a CO$_2$ partial pressure in the range of 10 to 55 bar and at a H$_2$ partial pressure in the range of 20 to 240 bar. Actually, the catalyst dissolved in the acidic medium is pressurised by a CO$_2$ partial pressure of 10 to 55 bar. Then the total gas pressure is increased up to a total pressure in the range of 30 to 250 with hydrogen gas, into the reaction vessel/container, in which the reaction is carried out. Thus the H$_2$ partial pressure to carry out said reaction is in the range 20 to 240 bar. In the method of the invention, the reaction is conducted at a total gas pressure of hydrogen and carbon dioxide being in the range of 30 to 250 bar. Said total gas pressure is preferably in the range of 60 to 100 bar. The other preferred range of the total gas pressure is of 55 to 180 bar, of 70 to 150 bar, and 100 to 170 bar. Preferably the total gas pressure is 100 bar.

The composition of the total gas pressure may be expressed as a ratio between the partial pressure of hydrogen gas and the partial pressure of carbon dioxide gas (P[H$_2$]/P[CO$_2$]). The reaction is conducted at a ratio between the partial pressure of hydrogen gas and the partial pressure of carbon dioxide gas (P[H$_2$]/P[CO$_2$]) being in the range of 1 to 9, or in the range of 1 to 3, preferably being 1.

The formic acid production strongly depends on the total gas pressure during the reaction of the method of the invention. An increase of the total gas pressure results in an increase of the final concentration of formic acid (see FIG. 1). The total gas pressure of the catalysed reaction may be set up and varied by the skilled person in order to obtain the yield of formic acid according to the conditions of the production or to the use of the produced formic acid on demand. For example, a turnover number (TON) corresponding to the number of moles of formic acid produced divided by the number of moles of catalyst, TON being about 520 is obtained at a total gas pressure of 200 bar with a concentration of catalyst of 0.100 mM, which is the highest TON obtained up to now in a reaction of direct hydrogenation of carbon dioxide in a pure acidic medium. The highest produced formic acid concentration is obtained at a total gas pressure of 200 bar and a concentration of catalyst of 2.76 m.

In a further embodiment, the catalysed reaction of the method of the invention is conducted in an acidic medium comprising water as polar solvent, at 60° C., at a total gas pressure of hydrogen and carbon dioxide of 200 bar, in the presence of a catalyst being $[RuCl_2(PTA)_4]$.

In a further embodiment, the catalysed reaction of the method of the invention is conducted in an acidic medium comprising DMSO as polar solvent, at 50° C., at a total gas pressure of hydrogen and carbon dioxide of 100 bar, in the presence of a catalyst being $[RuCl_2(PTA)_4]$. In these reaction conditions and for a concentration of catalyst of 2.8 mM, TON is 670.

The presence of formic acid influences the pH and the reaction of the present invention is preferably conducted at a pH in the range of 1.0 to 6.8. The pH may be in the range of 2.0 to 5.5, of 3.0 to 4.5, of 2.5 to 3.5 and preferably in the range of 1.5-3.5.

The temperature of the reaction was found to affect the rate and the yield of produced formic acid, since this reaction of $CO_2$ hydrogenation is exothermic. The increase of the temperature speeds up the rate of the formic acid formation (FIG. 2A and FIG. 2B) but has a negative effect on the final formic acid concentration. Accordingly, the catalysed reaction of the method of the present invention is preferably conducted at a temperature in the range of 15° C. to 140° C., of 30° C. to 100° C., preferably of 50° C. to 100° C. or 60° C. to 140° C., or more preferably at a temperature of 50° C. or 60° C.

The temperature is preferably applied from outside the reaction vessel by suitable heating/cooling equipment. For example, heat exchangers, electric heating, an oil bath and or water bath may be used to control the temperature in the interior of the reactor.

It is clear that the reaction temperatures can be controlled according to the preferences. If a high formic acid production is preferred, the reaction may be conducted at ambient temperatures for prolonged time, or low temperatures in the range of 20° C. to 50° C. or of 30° C. to 60° C. If the rate of the reaction is preferred, the temperature of the reaction is increased to the detriment of the quantity of produced formic acid. Temperature is thus one of the ways among others of controlling the reaction of the method of the present invention. By keeping the reaction vessel at a specific temperature, or by modifying this temperature, the reaction rate can conveniently be controlled.

A further way of controlling the reaction rate is, of course, the supply of hydrogen and carbon dioxide gases to the reaction vessel. The chemical reaction of the method of the present invention can be conducted batch-wise or continuously. In the batch-wise operation mode, the amount of formic acid produced per batch is determined by the amount of hydrogen and $CO_2$ gases being added at a total gas pressure in the range of 30 to 250 bar. In the continuous mode, the rate of adding hydrogen and carbon dioxide gases into the reaction vessel can be used to determine rate and/or amount of hydrogen being produced.

The method of the present invention can be controlled to produce a final concentration of free formic acid, namely not bound to the catalyst under the form of a salt or in presence of salts of at least 0.023 M, at least 0.050 M. Said method of the present invention can be controlled to produce from 0.023 M to 1.900 M from 0.080 M to 1.400 M, or from 0.200 M to 1.000 M of free formic acid according to the preference of the skilled person. Any value in the ranges may be obtained by adjusting parameters: the temperature, the total gas pressure, the choice of the polar solvent, the catalyst concentration, accordingly. Thus the yield of formic acid may be controlled to have a TON of at least 8.

The production of free formic acid in an acidic medium is an important advantage because the acid formic is readily available for the reverse reaction, namely the production of hydrogen gas and $CO_2$, which may be recycled, without the presence of carbon monoxide upon the demand of a hydrogen gas consuming device as described in EP 2086873. Thus according to the conditions described hereinabove, the reaction can be conveniently controlled providing important advantages, e.g. in combination with the requirements of a fuel cell.

Formic acid produced by the method of the invention, a direct hydrogenation of carbon dioxide in acidic medium, may be used for producing hydrogen gas by the method described in EP 2086873 or any other suitable method in a device or in a device capable of producing energy such as described in EP 2086873. The energy may be energy in any form, electric energy or heat.

The present invention provides a device for producing formic acid according to the method of the invention. Said device may be a container or a reactor, wherein the reaction of direct hydrogenation of carbon dioxide according to the method of the invention occurs and the produced formic acid is then provided to be stored in a container for any suitable use, for producing energy as being the reactant of a catalysed chemical reaction or for producing hydrogen gas using a catalyst.

The present invention is described more concretely with reference to the following examples, which, however, are not intended to restrict the scope of the invention.

EXAMPLES

Example 1

Preparation of Catalyst $[RuCl_2(PTA)_4]$ $[RuCl_2(PTA)_4]$ was synthesised as described in D. J. Darensbourg et al. (D. J. Darensbourg, F. Joo, M. Kannisto, A. Katho, J. H. Reibenspies, D. J. Daigle, Inorg Chem 1994, 33, 200).

To a stirred, warm slurry of PTA (1.89 g, 12 mmol) in 50 mL 96% ethanol was added, under nitrogen, a warm solution of $RuCl_3*H_2O$ (0.52 g, 2 mmol) in 25 mL of ethanol. The resulting mixture changed color in a few minutes from deep brown-red to light green-brown and was refluxed under nitrogen for 2 hours. After the mixture was cooled to ambient temperature, the resultant solid was filtered and washed with ethanol and acetone. The product, $RuCl_2(PTA)_4$, was dried under vacuum to afford 1.6 g (98% yield) of a yellow powder.

Example 2

Catalytic Hydrogenation of Carbon Dioxide Reaction

The catalytic hydrogenation of carbon dioxide is performed, by the dissolution of $[RuCl_2(PTA)_4]$ in 2 mL degassed water or in DMSO which is introduced in the sapphire NMR tube or in the autoclave under $N_2$ atmosphere. The solution is then pressurized up to 10-55 bar of $CO_2$ and then up to 60-200 bar total pressure with $H_2$. The system was heated between 23° C.-135° C. and stirred.

For sapphire NMR, the evolution of HCOOH and $CO_2$ is followed by $^1H$ or $^{13}C$ NMR with 3-(trimethylsilyl)-1-propanesulfonate (DSS) as an internal standard. For the autoclaves the final yield of formic acid is determined by $^1H$ NMR measurement of the product solution with sodium 3-(trimethylsilyl)-1-propanesulfonate (DSS) as standard (solution of 0.013 M). Determination and confirmation of final yield of formic acid is performed by NMR or by ionic chromatography.

All manipulations are carried out under oxygen-free conditions with degassed solvents, using Schlenk line techniques with $N_2$ protective gas. The reactions is carried out in medium-pressure sapphire NMR tubes (see I. T. Horvath, J. M. Millar, Chem Rev 1991, 91, 1339; A. Cusanelli, U. Frey, D. T. Richens, A. E. Merbach, J Am Chem Soc 1996, 118, 5265) up to 100 bar and is followed by $^1H$ and $^{13}C$ NMR spectrometry, at higher pressures Parr autoclaves were used. The NMR spectra are recorded on a Bruker DRX 400 NMR spectrometer and the fitting of the spectrum is done with the program WIN-NMR. The final formic concentration is determined from the NMR data as well as by ionic chromatography using the ICS-90 system.

Example 3

Effect of the Phosphine Ligand and the Metal Centre on the Catalyst [$RuCl_2(PTA)_4$] Reactivity According to the conditions mentioned in Example 2, the formation of formic acid is detected and its concentration is followed by $^1H$ NMR (singlet at 8.1 ppm, HCOOH), by $^{13}C$ NMR (doublet at 166 ppm, HCOOH), formic acid is the only product under these reaction conditions.

To understand the influence of the phosphine ligand and the metal centre on the reactivity of [$RuCl_2(PTA)_4$], some Ru, Rh and Ir catalysts active in aqueous condition are studied under the reaction conditions of 60 and 100 bar total pressure, $P(H_2)/P(CO_2)$ ratio of 1, reaction temperature of 60° C., 2.76 mM catalyst in a reaction volume of 2 mL ($H_2O$, DMSO), reaction time between 72-96 h. The data are average values of several (4-5) measurements and the reproducibility is 15% (see Table 1 and Table 2).

TABLE 1

Catalytic hydrogenation of $CO_2$ into HCOOH in water

| Entry | Catalyst precursor [mM] | Total pressure [bar] | HCOOH [mM] |
|---|---|---|---|
| 1 | [$RuCl_2(PTA)_4$] | 60 | 23 |
| 2 | [$RuCl_2(PTA)_4$] | 100 | 83 |
| 3 | [$RhCl(PTA)_3$] | 60 | 2 |
| 4 | [$RhCl(TPPMS)_3$] | 60 | 1 |
| 5 | [$RuCl_2(PTA)([9]aneS_3)$] | 60 | 13 |
| 6 | [$RuCl_2(PTA)([9]aneS_3)$] | 100 | 46 |
| 7 | [$RuCl_2(PTA)(C_6H_5(C_3H_8N))$] | 60 | 19 |
| 8 | [$RuCl_2(PTA)(C_6H_5(C_3H_8N))$] | 100 | 90 |
| 9 | [$RuCl_2(TPPMS)_2$] | 60 | 11 |
| 10 | [$RuCl_2(TPPMS)_2$] | 100 | 50 |
| 11 | [$RuCl_2(TPPTS)_2]_2$ | 60 | 12 |
| 12 | [$RuCl_2(p\text{-cymene})]_2$ | 60 | 12 |
| 13 | [$Ru(H_2O)_4(MePTA)_2](tos)_4$ | 60 | 29 |
| 14 | [$Ru(H_2O)_4(MePTA)_2](tos)_4$ | 100 | 111 |

The comparison of the metal centre shows that under acidic conditions, the ruthenium catalysts (Entries 3-4, Table 1) were in general 10 times more active than the rhodium catalysts. The effect of the PTA ligands is studied by the substitution of the PTA ligands by other phosphine ligands. Replacement of two of the PTA ligands by either the triethylene trisulfide ligand (Entries 5-6, Table 1) or by dimethylbenzylamine (Entries 7-8, Table 1), lead in both cases to the formation of formic acid.

It is interesting to note that, with [$RuCl_2(PTA)(C_6H_5(C_3H_8N))$], a formic acid concentration of 90 mM is reached. Kinetic studies of this catalyst have shown a similar behaviour than [$RuCl_2(PTA)_4$] (see FIGS. 3A and 3B, and FIGS. 4A and 4B). The replacement of all of the PTA ligands by TPPMS, TPPTS or p-cymene (Entries 9-12, Table 1) allows the production of formic acid but with a lower final concentration as for [$RuCl_2(PTA)([9]aneS_3)$]. These results show that the metal centre has an important effect on the catalytic hydrogenation of carbon dioxide, as well as of the presence of hydrophilic phosphine ligand.

TABLE 2

Catalytic hydrogenation of $CO_2$ into HCOOH in water or in DMSO

| Catalyst precursor | Total pressure [bar] | HCOOH in $H_2O$ [mM] | HCOOH in DMSO [mM] |
|---|---|---|---|
| [$RuCl_2(PTA)_4$] | 100 | 112 | 1'881 |
| [$RhCl(PTA)_3$] | 60 | 2 | — |
| [$RhCl(PTA)_3$] | 100 | — | 11 |
| [$RuCl_2(PTA)(C_6H_5(C_3H_8N))$] | 100 | 90 | 85 |
| $IrCl_3$ + 10 eq PTA | 100 | — | 2.7 |
| [$RuCl(p\text{-cymene})$] $(CH_2CHCH_2N_2C_3H_3CH_3)$ | 100 | 40 | 380 |

Example 4

Effect of the Pressure (Total or Partial) on Formic Acid Production with [$RuCl_2(PTA)_4$] Catalyst The influence of the pressure and of the catalyst concentration on the final formic acid production is studied and shown in Table 3.

Under mild conditions (60° C., 30 bar $CO_2$, 30 bar $H_2$, 2.76 mM [$RuCl_2(PTA)_4$] catalyst) and in aqueous solutions, [$RuCl_2(PTA)_4$] catalyzes the hydrogenation of $CO_2$ with a low reactivity leading to the formation of 30 mM HCOOH solution (Entry 1, see Table 3).

TABLE 3

Formic acid (HCOOH) formation as function of pressure and catalyst concentration in water

| Entry | Catalyst [mM] | Total Pressure [bar] | $P(H_2)/P(CO_2)$ | HCOOH [mM] |
|---|---|---|---|---|
| 1 | 2.76 | 60 | 1 | 30 |
| 2 | 2.76 | 70 | 1 | 42 |
| 3 | 2.76 | 80 | 1 | 47 |
| 4 | 2.76 | 100 | 1 | 83 |
| 5 | 2.76 | 100 | 2.5 | 86 |
| 6 | 2.76 | 100 | 4 | 70 |
| 7 | 2.76 | 120 | 1.5 | 95 |
| 8 | 2.76 | 150 | 2 | 124 |
| 9 | 2.76 | 200 | 3 | 204 |
| 10 | 0.63 | 100 | 1 | 100 |
| 11 | 5.46 | 100 | 1 | 70 |
| 12 | 0.63 | 60 | 1 | 35 |

TABLE 3-continued

Formic acid (HCOOH) formation as function of pressure and catalyst concentration in water

| Entry | Catalyst [mM] | Total Pressure [bar] | $P(H_2)/P(CO_2)$ | HCOOH [mM] |
|---|---|---|---|---|
| 13 | 5.46 | 60 | 1 | 29 |
| 14 | 0.107 | 200 | 3 | 56 |

(V = 2 ml water, temperature = 60° C., reaction time = 48-84 h until equilibrium, except no 14: Temperature 40° C., 400 hours, TON = 520)

The formic acid production strongly depends on the total gas pressure during the reaction. The influence of the total gas pressure with a ratio between hydrogen partial pressure and carbon dioxide partial pressure: $P(H_2)/P(CO_2)$ ratio of 1 (Table 3, Entries 1-4) shows that increasing the total gas pressure from 60 bar to 100 bar leads to an increase of the final concentration of HCOOH until 83 mM (Table 3, Entry 4). Higher concentrations are obtained by increasing the total gas pressure up to 200 bar (Table 3, Entries 4, 7-9 and FIG. 1), which promote formic acid production up to 204 mM. The direct production of 0.204 M formic acid is obtained at 200 bar of total gas pressure, using 50 bar of $CO_2$ and 150 bar partial pressure of $H_2$. The effect of the $P(H_2)/P(CO_2)$ ratio is further investigated (Table 3, Entries 4-6). The $P(H_2)/P(CO_2)$ ratio between 1 and 9 shows a small influence on the final formic acid concentration.

Example 5

Effect of the Temperature on Formic Acid Production with $RuCl_2$ PTA Catalyst

The experimental setting of Example 2 is modified to evaluate the effect of temperature on the pressure in the sapphire tube reactor.

Kinetic data as a function of the temperature is obtained by the study of the catalytic hydrogenation of $CO_2$ between 30° C. to 90° C. Using the sapphire NMR tubes (up to 100 bar), investigation on the temperature effect is done under the reaction conditions of 100 bar and 2.76 mM of $[RuCl_2(PTA)_4]$. As expected, the increase of the temperature speeds up the rate of the formic acid formation (FIGS. 2 A and B). The reaction conditions are 2.7 mM catalyst, total pressure of 100 bar, a ratio of partial pressure of $P(H_2)/P(CO_2)$ of 1 for a reaction volume of 2 mL (DSS solution of 0.013 M). The reproducibility is about 15%.

The highest turnover frequency (TOF=number of moles of $CO_2$ converted by the 1 mole of catalyst, divided by the total time, or the turnover number divided by time) is obtained in this study, using a catalyst concentration of 0.597 mM, pressurized in an autoclave at 135° C. under a total gas pressure of 120 bar for 10 minutes. The resulting formic acid concentration was of 24 mM which leads to a TOF of 246 $h^{-1}$.

Figure 2A:
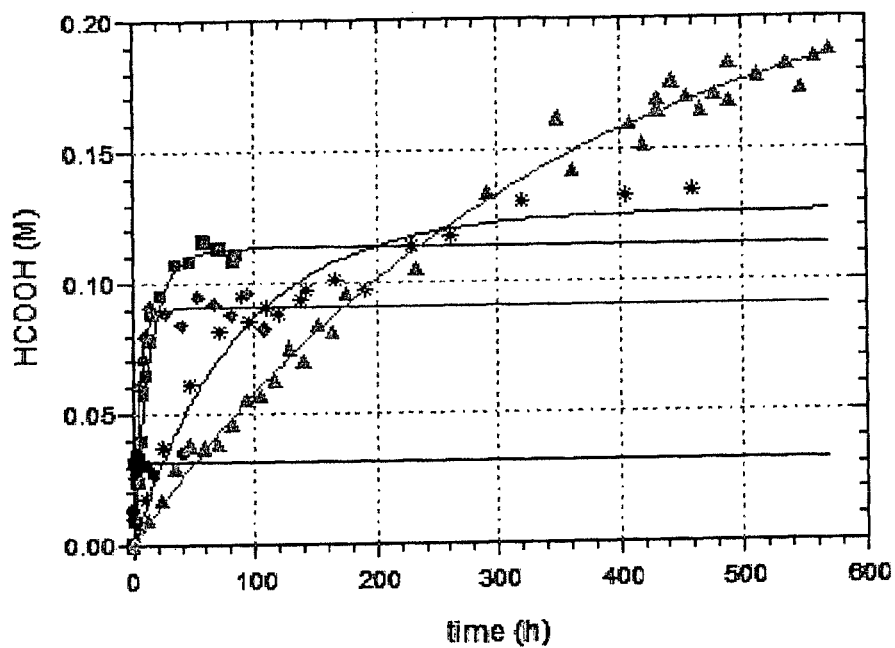
FIG. 2 shows the $CO_2$ hydrogenation into formic acid (HCOOH) with [$RuCl_2(PTA)_4$] catalyst at different temperatures 90° C. (circle); 60° C. (diamond); 50° C. (square), 40° C. (asterisk) and at 30° C. (triangle), FIG. 2A during 25 days, FIG. 2B during the first 3 days in water.
Figure 2B:
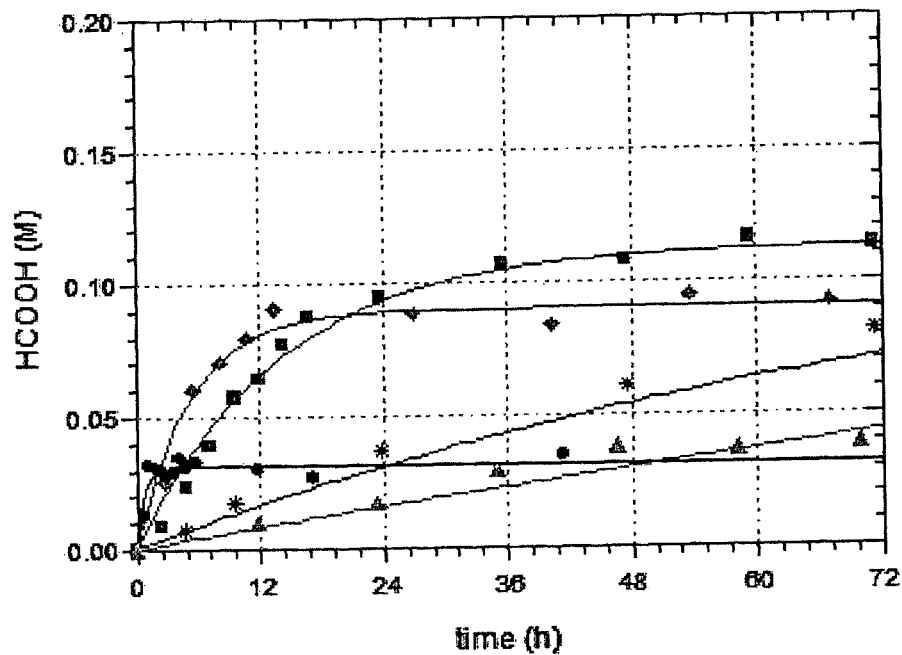
Figure 3A:
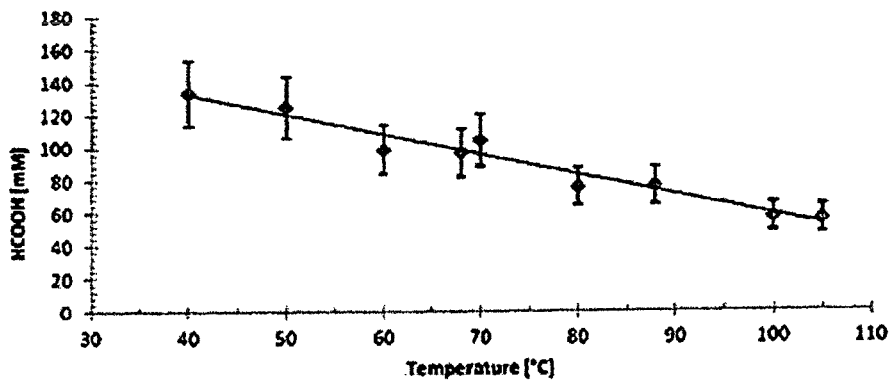
FIG. 3 shows the effect of the temperature (FIG. 3A) and of the pressure (FIG. 3B) on the catalytic hydrogenation of $CO_2$ with [$RuCl_2\{C_5H_5CH_2(CH_3)_2N\}(PTA)$] catalyst at 2.76 mM, at a reaction temperature=50° C., $P(H_2)/P(CO_2)$ ratio of 1 and a total pressure P(total)=100 bar pressure for FIG. 3A, in water.
Figure 3B:
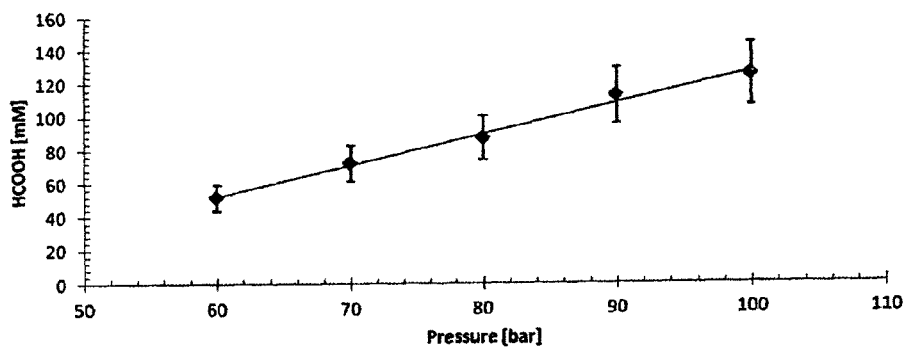
Figure 4A:
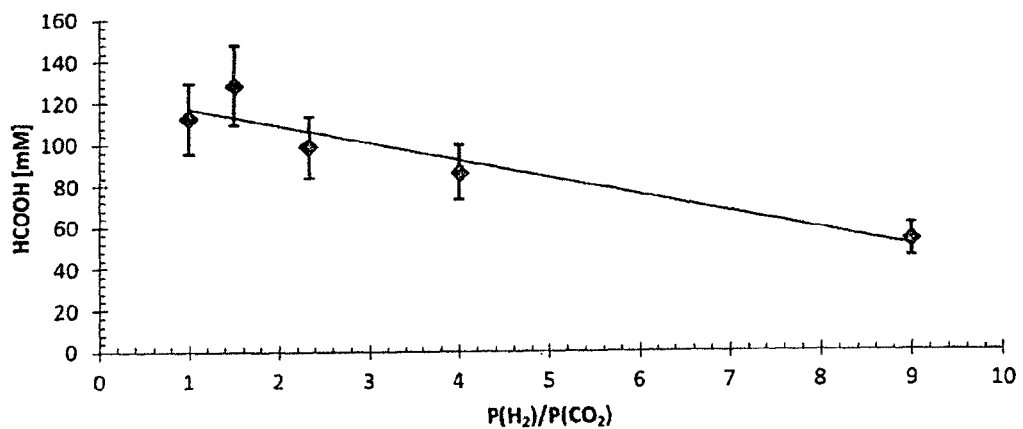
FIG. 4 shows the effect of the ratio between the hydrogen partial pressure and the carbon dioxide partial pressure [$P(H_2)/P(CO_2)$ ratio] (FIG. 4A) and effect of the catalyst concentration (FIG. 4B) on the catalytic hydrogenation of $CO_2$ with [$RuCl_2\{C_5H_5CH_2(CH_3)_2N\}(PTA)$] at a concentration from 1.13 to 5.36 mM, and 2.76 mM for FIG. 4A, at reaction temperature=50° C., P(total)=100 bar, $P(H_2)/P(CO_2)$ ratio in the range of 1 to 9 for FIG. 4A and of 1 for FIG. 4B, reaction time 144 h, in water.
Figure 4B:
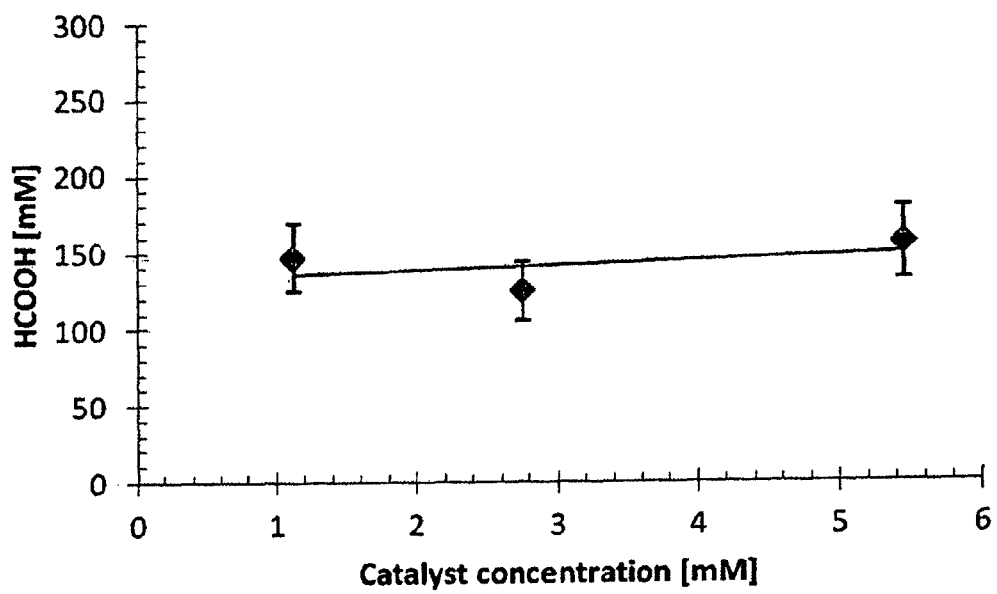

The increasing of the temperature has a negative effect on the final formic acid concentration which decreased from 186 mM at 30° C. to 32 mM at 90° C. (FIGS. 2A and 2B). These results can be explained by the exothermic reaction of $CO_2$ hydrogenation in water.

The experimental conditions investigated in this study which gave the highest concentration of 0.204 M formic acid, with a resulting TON of 74, are of 200 bar, 60° C. and 2.76 mM $[RuCl_2(PTA)_4]$. The highest TON was obtained by decreasing the $[RuCl_2(PTA)_4]$ concentration to 0.107 mM leading to a TON of 520 which is up to ten times higher than the 35 or 55 obtained by Ogo et al. with $[(\eta^6-C_6Me_6)Ru(L)(OH_2)]^{2+}$ (L=bpy or 4,4'-OMe-bpy).

Looking all the studied parameters, the optimal conditions for the final formic acid concentration were shown to be of 200 bar (50 bar $CO_2$ and 150 bar $H_2$), 60° C. and 0.628 mM $[RuCl_2(PTA)_4]$. In the other hands decreasing of the temperature to room temperature lead to an increase of the hydrogen production of 0.195 M but due to the slow reaction rate of the reaction further studies are difficult.

Example 6

Effect of the Temperature on Formic Acid Production with $[RuCl_2\{C_5H_5CH_2(CH_3)_2N\}(PTA)]$ Catalyst The experimental setting of Example 2 is modified to evaluate the effect of temperature on the pressure in the sapphire tube reactor with $[RuCl_2\{C_5H_5CH_2(CH_3)_2N\}(PTA)]$ catalyst instead of $[RuCl_2(PTA)_4]$ catalyst.

Figure 5A:
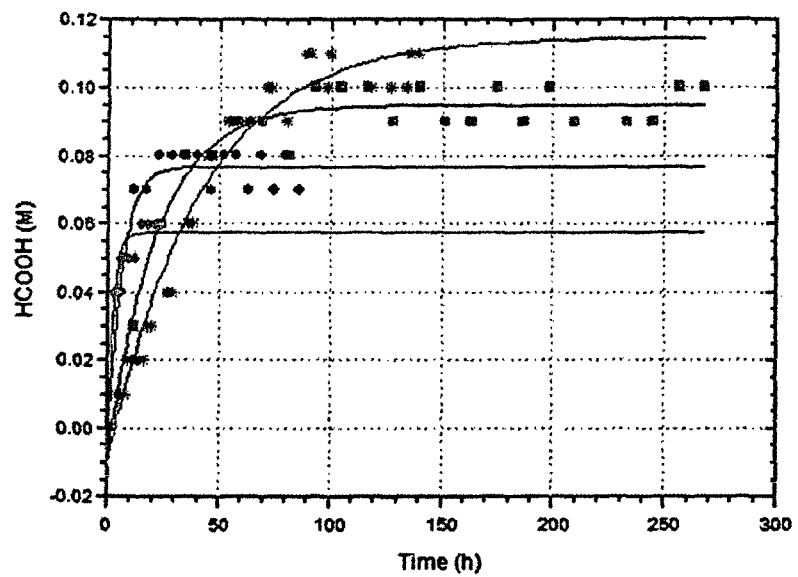
FIG. 5 shows $CO_2$ hydrogenation into formic acid (HCOOH) with [$RuCl_2\{C_5H_5CH_2(CH_3)_2N\}(PTA)$] catalyst at different temperatures 100° C. (diamond); 88° C. (circle); 68° C. (square), and at 60° C. (asterisk), FIG. 5A during 12 days, FIG. 5B during the first 2.5 days, in water.
Figure 5B:
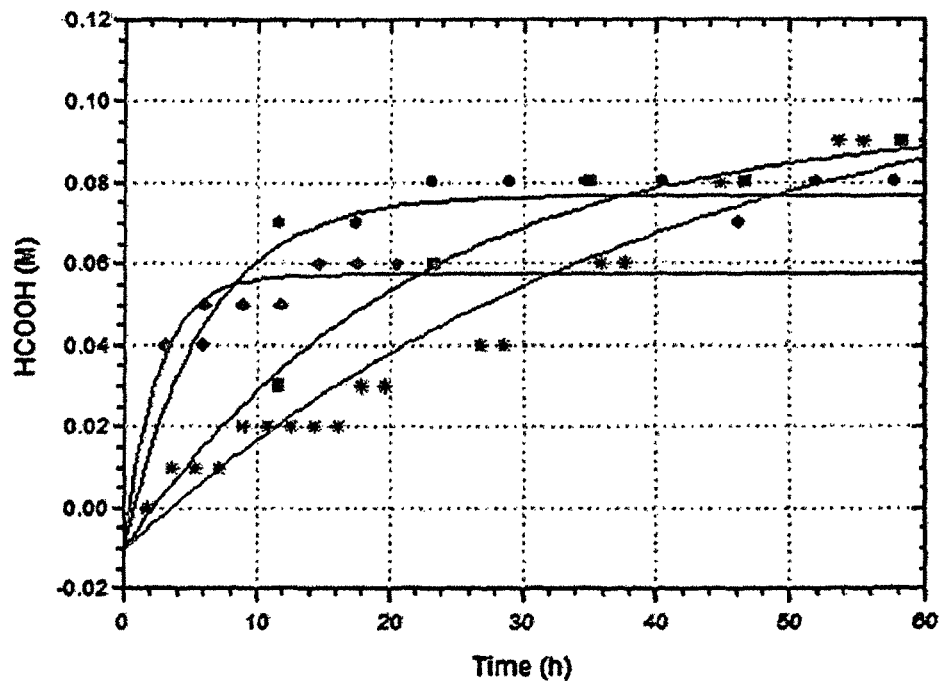

Kinetic data as a function of the temperature is obtained by the study of the catalytic hydrogenation of $CO_2$ between 40° C. to 100° C. Using the sapphire NMR tubes (from up to 100 bar), investigation on the temperature effect is done under the reaction conditions from 40 to 100 bar and 1.13 to 5.46 mM of $[RuCl_2\{C_5H_5CH_2(CH_3)_2N\}(PTA)]$. As expected, the increase of the temperature speeds up the rate of the formic acid formation (FIGS. 5 A and B) and decreases the quantity of produced formic acid (see Table 4). The reaction conditions are 1.13-5.46 mM catalyst, total pressure of 100 bar, a ratio of partial pressure of $P(H_2)/P(CO_2)$ of 1 to 9 for a reaction volume of 2 mL (DSS solution of 0.013 M). The reaction time is between 6 to 144 h depending of the temperature. The reproducibility is about 15%.

TABLE 4

Catalytic hydrogenation of $CO_2$ with $[RuCl_2\{C_5H_5CH_2(CH_3)_2N\}(PTA)]$ catalyst in water

| Entry | Catalyst concentration [mM] | Total pressure [bar] | Temperature [° C.] | $P(H_2)/P(CO_2)$ | HCOOH [mM] |
|---|---|---|---|---|---|
| 1 | 2.76 | 100 | 40 | 1 | 142 |
| 2 | 2.76 | 100 | 50 | 1 | 120 |
| 3 | 2.76 | 100 | 60 | 1 | 99 |
| 4 | 2.76 | 100 | 80 | 1 | 76 |
| 5 | 2.76 | 100 | 100 | 1 | 57 |
| 6 | 2.76 | 90 | 50 | 1 | 112 |
| 7 | 2.76 | 80 | 50 | 1 | 87 |
| 8 | 2.76 | 70 | 50 | 1 | 72 |
| 9 | 2.76 | 60 | 50 | 1 | 52 |
| 10 | 2.76 | 100 | 50 | 1.5 | 129 |
| 11 | 2.76 | 100 | 50 | 2.3 | 99 |
| 12 | 2.76 | 100 | 50 | 4 | 86 |
| 13 | 2.76 | 100 | 50 | 9 | 53 |
| 14 | 1.13 | 100 | 50 | 1 | 147 |
| 15 | 5.46 | 100 | 50 | 1 | 156 |

The invention claimed is:

1. A method for producing formic acid in a catalysed chemical reaction from hydrogen gas and carbon dioxide gas, said reaction being conducted:
   in an acidic medium comprising at least one polar solvent being DMSO;
   without any addition of a base and of at least a compound being formate ($HCOO^-$), carbonate ($CO_3^{2-}$), hydrogen carbonate ($HCO_3^-$) or any salt thereof;
   at a temperature in the range of 15-140° C.;

at a total gas pressure of hydrogen gas and carbon dioxide gas being in the range of 30 to 250 bar;

in the presence of a catalyst, said catalyst comprising a complex of the general formula (I):

$$MR_n(L1)_m(L2)_p \qquad (I)$$

wherein,

M is a metal being Ru, Rh, Ir or Fe;

R is Cl or $H_2O$;

L1 is an imidazolium pincer ligand or a phosphine ligand being aryl phosphines, alkyl phosphines or adamantylphosphine optionally comprising at least one heteroatom being N or O;

L2 is a ligand being tri-ethylene trisulfide, dimethylbenzylamine or para-cymene;

n, m and p are integer, wherein n is 1 or 2, m is in the range of 1-4 and p is in the range of 0-1; and wherein the complex of formula (I) optionally comprises further ligands different from L1 and L2 and is provided in the form of a salt or is neutral.

2. The method according to claim 1, wherein aryl phosphines are phenyl phosphines, diphenyl phosphines or triphenyl phosphines, which are further substituted by a hydrophilic group being sulphonate, carboxylate and/or hydroxyl.

3. The method according to claim 2, wherein the hydrophilic group is sulphonate and the aryl phosphine is mono-, di- or trisulphonated aryl phosphine.

4. The method according to claim 1, wherein L1 is at least one ligand being 1,3,5-triaza-7-phosphaadamantane (PTA), substituted PTA, 3-methyl-1,3,7-triaza-5-phosphabicyclo[3.3.1]nonane (MePTA); meta-monosulfonated triphenylphosphine (TPPMS) or meta-trisulfonated triphenylphosphine (TPPTS).

5. The method according to claim 1, wherein the reaction is conducted at a temperature in the range of 30-100° C.

6. The method according to claim 1, wherein the reaction is conducted at a total gas pressure of hydrogen and carbon dioxide being in the range of 60-100 bar.

7. The method according to claim 1, wherein the reaction is conducted at a $H_2$ partial pressure in the range of 10-240 bar.

8. The method according to claim 1, wherein M is Ru or Fe.

9. The method according to claim 1, wherein the catalyst is $[RuCl_2(PTA)_4]$, $[RuCl_2(PTA)([9]aneS_3)]$, $[RuCl_2(PTA)(C_6H_5(C_3H_8N))]$, $[Ru(H_2O)_4(MePTA)_2](tos)_4$ or $[RuCl_2(TPPMS)_2]$.

* * * * *